United States Patent
Alam et al.

(10) Patent No.: US 10,213,532 B2
(45) Date of Patent: *Feb. 26, 2019

(54) PORTABLE HAND PUMP FOR EVACUATION OF FLUIDS

(71) Applicant: The Henry M. Jackson Foundation for the Advancement of Military Medicine, Inc., Bethesda, MD (US)

(72) Inventors: Hasan B. Alam, Ann Arbor, MI (US); Peter Rhee, Tucson, AZ (US); Emily Rhee, Tucson, AZ (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/912,244

(22) Filed: Mar. 5, 2018

(65) Prior Publication Data

US 2018/0256789 A1    Sep. 13, 2018

Related U.S. Application Data

(60) Continuation of application No. 15/210,787, filed on Jul. 14, 2016, now Pat. No. 9,907,887, which is a (Continued)

(51) Int. Cl.
*A61M 1/00* (2006.01)
*A61M 27/00* (2006.01)
(Continued)

(52) U.S. Cl.
CPC ........ *A61M 1/0021* (2013.01); *A61M 1/0003* (2013.01); *A61M 1/0011* (2013.01);
(Continued)

(58) Field of Classification Search
CPC ......... A61M 1/00; A61M 27/00; A61F 13/00; A61F 13/02
See application file for complete search history.

(56) References Cited

U.S. PATENT DOCUMENTS

| | | | |
|---|---|---|---|
| 2,547 | A | 4/1842 | Welchman |
| 11,623 | A | 8/1854 | Waters |
| (Continued) | | | |

FOREIGN PATENT DOCUMENTS

| | | |
|---|---|---|
| CA | 2546434 | 1/2013 |
| DE | 1616493 | 6/1971 |
| (Continued) | | |

OTHER PUBLICATIONS

Office Action dated Sep. 18, 2015 for U.S. Appl. No. 14/464,503.
(Continued)

*Primary Examiner* — Tatyana Zalukaeva
*Assistant Examiner* — Ilya Treyger
(74) *Attorney, Agent, or Firm* — Stoel Rives LLP

(57) ABSTRACT

A manually operable pump for the effective removal of fluids to include blood, blood clots, fluid, and air from a body cavity of a subject is provided. The manually operable pump is adapted to be connect to a range of fluid conduits and is equipped with one-way valves that effectively permit flow of fluid through the pump in only one direction. The sensitivity of the one-way valves is such that when properly positioned, fluid can flow through the valves and out of the pump without manual compression of the pump and with the aid of gravity power alone.

20 Claims, 2 Drawing Sheets

Direction of flow →

Related U.S. Application Data division of application No. 14/162,654, filed on Jan. 23, 2014, now Pat. No. 9,393,353, which is a division of application No. 10/595,450, filed as application No. PCT/US2004/038937 on Nov. 22, 2004, now Pat. No. 8,636,721.

(60) Provisional application No. 60/523,321, filed on Nov. 20, 2003.

(51) Int. Cl.
| | | |
|---|---|---|
| *B21B 28/04* | (2006.01) | |
| *B24B 5/04* | (2006.01) | |
| *B24B 5/37* | (2006.01) | |
| *B24D 3/14* | (2006.01) | |
| *B24D 5/00* | (2006.01) | |
| *A61M 1/04* | (2006.01) | |
| *A61M 16/04* | (2006.01) | |
| *A61M 39/24* | (2006.01) | |
| *A61F 13/00* | (2006.01) | |
| *A61F 13/02* | (2006.01) | |

(52) U.S. Cl.
CPC ........ *A61M 1/0023* (2013.01); *A61M 1/0066* (2013.01); *A61M 1/04* (2013.01); *A61M 16/0463* (2013.01); *A61M 27/00* (2013.01); *A61M 39/24* (2013.01); *B21B 28/04* (2013.01); *B24B 5/04* (2013.01); *B24B 5/37* (2013.01); *B24D 3/14* (2013.01); *B24D 5/00* (2013.01); *A61M 2205/071* (2013.01); *A61M 2205/078* (2013.01)

(56) References Cited

U.S. PATENT DOCUMENTS

| | | |
|---|---|---|
| 44,843 A | 10/1864 | Smith |
| 527,653 A | 10/1894 | Bienz |
| 530,951 A | 12/1894 | LaPointe et al. |
| 585,349 A | 6/1897 | Eisfeld |
| 670,895 A | 3/1901 | Esmond |
| 733,496 A | 7/1903 | Lyons |
| 1,177,208 A | 3/1916 | Pierpont |
| 1,197,232 A | 9/1916 | Pierpont |
| 2,397,257 A | 3/1946 | Goland et al. |
| 3,003,500 A | 10/1961 | Barton et al. |
| 3,021,841 A | 2/1962 | Burke |
| 3,058,627 A | 10/1962 | Eskridge |
| 3,115,138 A | 12/1963 | McElvenny et al. |
| 3,223,610 A | 12/1965 | Inoue |
| 3,233,610 A | 2/1966 | Wade |
| 3,241,554 A | 3/1966 | Coanda |
| 3,253,594 A | 5/1966 | Matthews |
| 3,312,221 A | 4/1967 | Overment |
| 3,315,802 A | 4/1967 | Lonholdt et al. |
| 3,319,684 A | 5/1967 | Calhoun |
| 3,340,869 A | 9/1967 | Bane |
| 3,363,626 A | 1/1968 | Bidwell et al. |
| 3,376,868 A | 4/1968 | Mondiadis |
| 3,417,750 A | 12/1968 | Carson |
| 3,419,010 A | 12/1968 | Williamson |
| 3,459,189 A | 8/1969 | Alley |
| 3,487,837 A | 1/1970 | Petersen |
| 3,542,026 A | 11/1970 | Bledsoe |
| 3,554,580 A | 1/1971 | Goyke |
| 3,566,875 A | 3/1971 | Stoehr |
| 3,572,340 A | 3/1971 | Lloyd et al. |
| 3,650,507 A | 3/1972 | Nyberg et al. |
| 3,680,562 A | 8/1972 | Wittes et al. |
| 3,683,929 A | 8/1972 | Holter |
| 3,742,952 A | 7/1973 | Magers et al. |
| 3,752,158 A | 8/1973 | Kariher |
| 3,768,476 A | 10/1973 | Raitto |
| 3,774,611 A | 12/1973 | Tussey et al. |
| 3,777,757 A | 12/1973 | Gray et al. |
| 3,809,087 A | 5/1974 | Lewis |
| 3,820,546 A | 6/1974 | Chittenden et al. |
| 3,853,127 A | 12/1974 | Spademan |
| 3,875,941 A | 4/1975 | Adair |
| 3,920,023 A | 11/1975 | Dye et al. |
| 3,960,153 A | 6/1976 | Carey et al. |
| 3,982,546 A | 9/1976 | Friend |
| 4,022,209 A | 5/1977 | Nehring |
| 4,029,095 A | 6/1977 | Pena |
| 4,073,294 A | 2/1978 | Stanley et al. |
| 4,105,031 A | 8/1978 | Kurtz et al. |
| 4,112,949 A | 9/1978 | Rosenthal et al. |
| 4,116,366 A | 9/1978 | Takenakashima et al. |
| 4,120,715 A | 10/1978 | Ockwell et al. |
| 4,143,853 A | 3/1979 | Abramson |
| 4,136,696 A | 5/1979 | Nehring |
| 4,153,058 A | 5/1979 | Nehme |
| 4,170,300 A | 10/1979 | Pick |
| 4,174,053 A | 11/1979 | Shimizu |
| 4,187,848 A | 2/1980 | Taylor |
| 4,203,445 A | 5/1980 | Jessup et al. |
| 4,214,593 A | 7/1980 | Imbruce et al. |
| 4,257,629 A | 3/1981 | Maple et al. |
| 4,265,848 A | 5/1981 | Rusch et al. |
| 4,266,355 A | 5/1981 | Moss |
| 4,266,545 A | 5/1981 | Moss |
| 4,310,104 A | 1/1982 | Takatsuki |
| 4,315,513 A | 2/1982 | Nawash et al. |
| 4,334,551 A | 6/1982 | Pfister |
| 4,341,212 A | 7/1982 | Medwid |
| D267,433 S | 12/1982 | Pageau |
| 4,364,395 A | 12/1982 | Redmond et al. |
| D267,815 S | 2/1983 | Elliott et al. |
| 4,382,442 A | 5/1983 | Jones |
| 4,392,858 A | 7/1983 | George et al. |
| 4,393,873 A | 7/1983 | Nawash et al. |
| 4,396,382 A | 8/1983 | Goldhaber |
| 4,402,682 A | 9/1983 | Garver, Sr. et al. |
| 4,421,146 A | 12/1983 | Bond et al. |
| 4,427,425 A | 1/1984 | Briggs et al. |
| 4,429,693 A | 2/1984 | Blake et al. |
| 4,433,973 A | 2/1984 | Kurtz et al. |
| 4,439,190 A | 3/1984 | Protzmann et al. |
| 4,447,235 A | 5/1984 | Clarke |
| 4,455,141 A | 6/1984 | Todd |
| 4,464,168 A | 8/1984 | Redmond et al. |
| 4,475,904 A | 10/1984 | Wang |
| 4,479,818 A | 10/1984 | Briggs et al. |
| 4,490,003 A | 12/1984 | Robinson |
| 4,496,464 A | 1/1985 | Hensley |
| 4,501,363 A | 2/1985 | Isbey, Jr. |
| 4,511,163 A | 4/1985 | Harris et al. |
| 4,512,771 A | 4/1985 | Norton |
| 4,525,167 A | 6/1985 | Goldberg et al. |
| 4,539,985 A | 9/1985 | Magrath |
| 4,543,100 A | 9/1985 | Brodsky |
| 4,564,222 A | 1/1986 | Loker et al. |
| 4,569,674 A | 2/1986 | Phillips et al. |
| 4,583,972 A | 4/1986 | Hunter, III et al. |
| 4,605,400 A | 8/1986 | Kurtz et al. |
| 4,610,469 A | 9/1986 | Wolff-Mooij |
| 4,610,671 A | 9/1986 | Luther |
| 4,620,846 A | 11/1986 | Goldberg et al. |
| 4,642,088 A | 2/1987 | Gunter |
| 4,643,720 A | 2/1987 | Lanciano |
| 4,648,870 A | 3/1987 | Goldberg et al. |
| 4,666,433 A | 5/1987 | Parks |
| 4,669,463 A | 6/1987 | McConnell |
| 4,673,398 A | 6/1987 | Turner et al. |
| 4,675,020 A | 6/1987 | McPhee |
| 4,681,571 A | 7/1987 | Nehring |
| 4,685,901 A | 8/1987 | Parks |
| 4,685,908 A | 8/1987 | Kurtz |
| 4,701,163 A | 10/1987 | Parks |
| 4,702,733 A | 10/1987 | Wright et al. |
| 4,706,830 A | 11/1987 | Wareing |
| 4,722,735 A | 2/1988 | Brodmann |

(56) References Cited

U.S. PATENT DOCUMENTS

| | | |
|---|---|---|
| 4,738,671 A | 4/1988 | Elliott et al. |
| 4,740,202 A | 4/1988 | Stacey et al. |
| 4,741,678 A | 5/1988 | Nehring |
| 4,747,843 A | 5/1988 | Felix et al. |
| 4,747,844 A | 5/1988 | Elliott |
| 4,752,292 A | 6/1988 | Lopez et al. |
| 4,758,238 A | 7/1988 | Sundblom et al. |
| 4,781,674 A | 11/1988 | Redmond et al. |
| 4,790,567 A | 12/1988 | Kawano et al. |
| 4,809,679 A | 3/1989 | Shimonaka et al. |
| 4,813,929 A | 3/1989 | Semrad |
| 4,820,288 A | 4/1989 | Isono |
| 4,828,546 A | 5/1989 | McNeil et al. |
| 4,832,442 A | 5/1989 | Pappas |
| 4,834,702 A | 5/1989 | Rocco |
| 4,844,087 A | 7/1989 | Garg |
| 4,850,955 A | 7/1989 | Newkirk |
| 4,857,042 A | 8/1989 | Schneider |
| 4,857,072 A | 8/1989 | Schneider |
| 4,863,593 A | 9/1989 | Quick |
| 4,867,740 A | 9/1989 | East |
| 4,874,377 A | 10/1989 | Newgard et al. |
| 4,883,474 A | 11/1989 | Sheridan et al. |
| 4,883,476 A | 11/1989 | Kurtz et al. |
| 4,921,468 A | 5/1990 | Maitz et al. |
| 4,928,830 A | 5/1990 | Brewer |
| 4,929,235 A | 5/1990 | Merry et al. |
| 4,930,997 A | 6/1990 | Bennett |
| 4,936,837 A | 6/1990 | Wexler |
| 4,944,732 A | 7/1990 | Russo |
| 4,946,448 A | 8/1990 | Richmond |
| 4,946,449 A | 8/1990 | Davis, Jr. |
| 4,949,756 A | 8/1990 | Melinyshyn et al. |
| 4,950,256 A | 8/1990 | Luther et al. |
| 4,960,412 A | 10/1990 | Fink |
| 4,966,197 A | 10/1990 | Jaron et al. |
| 4,968,294 A | 11/1990 | Salama |
| 4,969,879 A | 11/1990 | Lichte |
| 4,969,890 A | 11/1990 | Sugita et al. |
| 4,973,311 A | 11/1990 | Iwakoshi et al. |
| 4,981,474 A | 1/1991 | Bopp et al. |
| 4,995,864 A | 2/1991 | Bartholomew et al. |
| 5,002,528 A | 3/1991 | Palestrant |
| 5,002,529 A | 3/1991 | Cunningham |
| 5,009,226 A | 4/1991 | Holt |
| 5,009,635 A | 4/1991 | Scarberry |
| 5,009,636 A | 4/1991 | Wortley et al. |
| 5,019,059 A | 5/1991 | Goldberg et al. |
| 5,019,096 A | 5/1991 | Fox, Jr. et al. |
| 5,024,653 A | 6/1991 | Kohnka |
| 5,037,403 A | 8/1991 | Garcia |
| 5,048,875 A | 9/1991 | Usui et al. |
| 5,052,998 A | 10/1991 | Zimmon |
| 5,053,014 A | 10/1991 | Van Heugten |
| 5,057,084 A | 10/1991 | Ensminger et al. |
| 5,060,833 A | 10/1991 | Edison et al. |
| 5,061,255 A | 10/1991 | Greenfeld et al. |
| 5,062,835 A | 11/1991 | Maitz et al. |
| 5,064,416 A | 11/1991 | Newgard et al. |
| 5,078,677 A | 1/1992 | Gentelia et al. |
| 5,078,689 A | 1/1992 | Keller |
| 5,078,699 A | 1/1992 | Haber et al. |
| 5,085,349 A | 2/1992 | Fawcett |
| 5,092,850 A | 3/1992 | Buma |
| 5,098,405 A | 3/1992 | Peterson et al. |
| 5,100,394 A | 3/1992 | Dudar et al. |
| 5,102,404 A | 4/1992 | Goldberg et al. |
| 5,106,054 A | 4/1992 | Mollenauer et al. |
| 5,112,323 A | 5/1992 | Winkler et al. |
| 5,123,677 A | 6/1992 | Kreczko et al. |
| 5,137,524 A | 8/1992 | Lynn et al. |
| 5,141,499 A | 8/1992 | Zappacosta |
| 5,156,597 A | 10/1992 | Verreet et al. |
| 5,165,953 A | 11/1992 | Shlenker et al. |
| 5,165,963 A | 11/1992 | Shlenker et al. |
| 5,188,622 A | 2/1993 | Muller et al. |
| 5,199,946 A | 4/1993 | Abramowitz |
| 5,207,655 A | 5/1993 | Sheridan |
| 5,215,538 A | 6/1993 | Larkin |
| 5,234,454 A | 8/1993 | Bangs |
| 5,238,217 A | 8/1993 | Fell |
| 5,242,422 A | 9/1993 | Schneberger et al. |
| 5,251,873 A | 10/1993 | Atkinson et al. |
| 5,261,897 A | 11/1993 | Kurtz et al. |
| 5,269,771 A | 12/1993 | Thomas et al. |
| 5,279,551 A | 1/1994 | James |
| 5,279,601 A | 1/1994 | Lichte |
| 5,280,876 A | 1/1994 | Atkins |
| 5,295,657 A | 3/1994 | Atkinson |
| 5,295,658 A | 3/1994 | Atkinson et al. |
| 5,300,034 A | 4/1994 | Behnke et al. |
| 5,300,048 A | 4/1994 | Drewes, Jr. et al. |
| 5,304,121 A | 4/1994 | Sahatjian |
| 5,309,924 A | 5/1994 | Peabody |
| 5,320,110 A | 6/1994 | Wang |
| 5,322,518 A | 6/1994 | Schneider et al. |
| 5,330,447 A | 7/1994 | Barth |
| 5,334,159 A | 8/1994 | Turkel |
| 5,334,166 A | 8/1994 | Palestrant |
| 5,344,401 A | 9/1994 | Radisch et al. |
| 5,345,929 A | 9/1994 | Jansson et al. |
| 5,352,198 A | 10/1994 | Goldenberg et al. |
| 5,356,391 A | 10/1994 | Stewart |
| 5,360,413 A | 11/1994 | Leason et al. |
| 5,390,898 A | 2/1995 | Smedley et al. |
| 5,395,651 A | 3/1995 | Sodervall et al. |
| 5,399,165 A | 3/1995 | Paul, Jr. |
| 5,401,245 A | 3/1995 | Haining |
| 5,401,363 A | 3/1995 | Begemann |
| 5,403,284 A | 4/1995 | Gross |
| 5,405,331 A | 4/1995 | Bahnke et al. |
| 5,407,434 A | 4/1995 | Gross |
| 5,423,334 A | 6/1995 | Jordan |
| 5,435,470 A | 7/1995 | Kim |
| 5,437,900 A | 8/1995 | Kuzowski |
| 5,456,675 A | 10/1995 | Wolbring et al. |
| 5,465,857 A | 11/1995 | Yang |
| 5,470,319 A | 11/1995 | Mayer |
| 5,472,325 A | 12/1995 | Svendsen |
| 5,472,435 A | 12/1995 | Sutton |
| 5,480,392 A | 1/1996 | Mous |
| 5,484,401 A | 1/1996 | Rodriguez |
| 5,489,269 A | 2/1996 | Aldrich et al. |
| 5,492,304 A | 2/1996 | Smith et al. |
| 5,496,299 A | 3/1996 | Felix et al. |
| 5,501,426 A | 3/1996 | Atkinson et al. |
| 5,505,717 A | 4/1996 | Moore |
| 5,507,733 A | 4/1996 | Larkin |
| 5,507,847 A | 4/1996 | George et al. |
| 5,509,433 A | 4/1996 | Paradis |
| 5,509,909 A | 4/1996 | Moy |
| 5,509,912 A | 4/1996 | Vaillancourt et al. |
| 5,514,117 A | 5/1996 | Lynn |
| 5,520,665 A | 5/1996 | Fleetwood et al. |
| 5,529,278 A | 6/1996 | Weldon et al. |
| 5,535,785 A | 7/1996 | Werge et al. |
| 5,540,661 A | 7/1996 | Tomisaka et al. |
| 5,556,387 A | 9/1996 | Mollenauer et al. |
| 5,573,516 A | 11/1996 | Tyner |
| 5,576,072 A | 11/1996 | Hostettler et al. |
| 5,597,536 A | 1/1997 | Mayer |
| 5,628,735 A | 5/1997 | Skow |
| 5,628,908 A | 5/1997 | Kamen et al. |
| 5,636,875 A | 6/1997 | Wasser et al. |
| 5,637,103 A | 6/1997 | Kerwin et al. |
| 5,662,960 A | 9/1997 | Hostettler et al. |
| 5,674,192 A | 10/1997 | Sahatjian et al. |
| 5,676,346 A | 10/1997 | Leinsing |
| D385,889 S | 11/1997 | Kullas et al. |
| 5,685,866 A | 11/1997 | Lopez |
| 5,690,612 A | 11/1997 | Lopez et al. |
| 5,695,466 A | 12/1997 | Lopez et al. |
| 5,701,934 A | 12/1997 | Kuran et al. |
| 5,709,672 A | 1/1998 | Illner |

(56) References Cited

U.S. PATENT DOCUMENTS

| | | |
|---|---|---|
| 5,725,506 A | 3/1998 | Freeman et al. |
| 5,727,714 A | 3/1998 | Fawcett |
| 5,733,496 A | 3/1998 | Avellanet |
| 5,735,826 A | 4/1998 | Richmond |
| 5,738,144 A | 4/1998 | Rogers |
| 5,738,656 A | 4/1998 | Wagner |
| 5,745,719 A | 4/1998 | Falcon et al. |
| 5,746,719 A | 5/1998 | Farra et al. |
| 5,776,119 A | 7/1998 | Bilbo et al. |
| 5,792,098 A | 8/1998 | Felix et al. |
| 5,792,108 A | 8/1998 | Felix et al. |
| 5,807,348 A | 9/1998 | Zinger et al. |
| 5,810,792 A | 9/1998 | Fangrow, Jr. et al. |
| 5,813,597 A | 9/1998 | Wakevainen |
| 5,814,024 A | 9/1998 | Thompson et al. |
| 5,823,961 A | 10/1998 | Fields et al. |
| 5,830,185 A | 11/1998 | Block, Jr. |
| 5,839,715 A | 11/1998 | Leinsing |
| 5,873,853 A | 2/1999 | Keilman et al. |
| 5,897,782 A | 4/1999 | Chatelin et al. |
| 5,904,334 A | 5/1999 | Grunert et al. |
| 5,921,972 A | 7/1999 | Skow |
| 5,937,885 A | 8/1999 | Sampson |
| 5,938,176 A | 8/1999 | Falconer |
| 5,944,703 A | 8/1999 | Dixon et al. |
| 5,947,953 A | 9/1999 | Ash et al. |
| 5,954,313 A | 9/1999 | Ryan |
| 5,954,706 A | 9/1999 | Sahatjian |
| 5,957,898 A | 9/1999 | Jepson et al. |
| 5,957,912 A | 9/1999 | Heitzmann |
| 5,961,497 A | 10/1999 | Larkin |
| 5,971,357 A | 10/1999 | Denton et al. |
| 5,972,441 A | 10/1999 | Campbell et al. |
| 5,976,650 A | 11/1999 | Campbell et al. |
| 5,984,891 A | 11/1999 | Keilman et al. |
| 5,997,486 A | 12/1999 | Burek et al. |
| 6,001,079 A | 12/1999 | Pourchez |
| 6,024,731 A | 2/2000 | Seddon et al. |
| 6,025,044 A | 2/2000 | Campbell et al. |
| 6,027,779 A | 2/2000 | Campbell et al. |
| 6,027,811 A | 2/2000 | Campbell et al. |
| 6,029,946 A | 2/2000 | Doyle |
| 6,039,302 A | 3/2000 | Cote, Sr. et al. |
| 6,039,714 A | 3/2000 | Cracauer et al. |
| 6,056,730 A | 5/2000 | Greter |
| 6,056,731 A | 5/2000 | Koetke et al. |
| 6,063,062 A | 5/2000 | Paradis |
| 6,068,011 A | 5/2000 | Paradis |
| 6,070,767 A | 6/2000 | Gardner et al. |
| 6,079,444 A | 6/2000 | Harris et al. |
| 6,089,541 A | 7/2000 | Weinheimer et al. |
| 6,093,154 A | 7/2000 | Burek et al. |
| 6,103,695 A | 8/2000 | Lane et al. |
| 6,106,502 A | 8/2000 | Richmond |
| 6,106,503 A | 8/2000 | Pfeiderer et al. |
| 6,113,068 A | 9/2000 | Ryan |
| 6,117,114 A | 9/2000 | Paradis |
| 6,120,264 A | 9/2000 | Wang |
| 6,129,699 A | 10/2000 | Haight et al. |
| 6,129,750 A | 10/2000 | Tockman et al. |
| 6,132,403 A | 10/2000 | Lopez |
| 6,132,407 A | 10/2000 | Genese et al. |
| 6,149,129 A | 11/2000 | Harris et al. |
| 6,156,004 A | 12/2000 | Tremaine et al. |
| 6,165,217 A | 12/2000 | Hayes |
| 6,168,137 B1 | 1/2001 | Paradis |
| 6,170,800 B1 | 1/2001 | Meloul et al. |
| 6,171,287 B1 | 1/2001 | Lynn et al. |
| 6,193,682 B1 | 2/2001 | Ahmed |
| 6,196,992 B1 | 3/2001 | Keilman et al. |
| 6,200,292 B1 | 3/2001 | French et al. |
| 6,217,556 B1 | 4/2001 | Ellingson et al. |
| 6,221,425 B1 | 4/2001 | Michal et al. |
| 6,234,992 B1 | 5/2001 | Haight et al. |
| 6,235,009 B1 | 5/2001 | Skow |
| 6,245,048 B1 | 6/2001 | Fangrow, Jr. et al. |
| 6,254,061 B1 | 7/2001 | Levine et al. |
| 6,254,581 B1 | 7/2001 | Scott |
| 6,261,276 B1 | 7/2001 | Reitsma |
| 6,261,282 B1 | 7/2001 | Jepson et al. |
| 6,283,949 B1 | 9/2001 | Roorda |
| 6,287,285 B1 | 9/2001 | Michal et al. |
| 6,293,929 B1 | 9/2001 | Smith et al. |
| 6,299,131 B1 | 10/2001 | Ryan |
| 6,299,593 B1 | 10/2001 | Wakabayashi |
| 6,309,423 B2 | 10/2001 | Hayes |
| 6,319,235 B1 | 11/2001 | Yoshimo |
| 6,328,765 B1 | 12/2001 | Hardwick et al. |
| 6,332,892 B1 | 12/2001 | Desmond, III et al. |
| 6,344,033 B1 | 2/2002 | Jepson et al. |
| 6,352,525 B1 | 3/2002 | Wakabayashi |
| 6,375,024 B1 | 4/2002 | Park |
| 6,391,009 B1 | 5/2002 | Crosa Dorado |
| 6,409,716 B1 | 6/2002 | Sahatiian et al. |
| 6,428,520 B1 | 8/2002 | Lopez et al. |
| 6,447,473 B1 | 9/2002 | Levine et al. |
| 6,468,190 B1 | 10/2002 | Fazio et al. |
| 6,482,190 B1 | 11/2002 | Genese et al. |
| 6,491,668 B1 | 12/2002 | Paradis |
| 6,500,164 B1 | 12/2002 | Turner et al. |
| 6,530,951 B1 | 3/2003 | Bates et al. |
| 6,541,116 B2 | 4/2003 | Michal et al. |
| 6,551,267 B1 | 4/2003 | Cohen et al. |
| 6,554,808 B1 | 4/2003 | Cook |
| 6,562,013 B1 | 5/2003 | Marasco, Jr. |
| RE38,145 E | 6/2003 | Lynn |
| 6,620,132 B1 | 9/2003 | Skow |
| 6,626,418 B2 | 9/2003 | Kiehne et al. |
| 6,629,707 B1 | 10/2003 | Yamaguchi et al. |
| 6,634,384 B2 | 10/2003 | Skeens et al. |
| 6,635,020 B2 | 10/2003 | Tripp, Jr. et al. |
| 6,637,726 B1 | 10/2003 | Yamamoto |
| 6,641,562 B1 | 11/2003 | Peterson |
| 6,641,574 B2 | 11/2003 | Badia Segura et al. |
| 6,645,547 B1 | 11/2003 | Shekalim et al. |
| 6,651,956 B2 | 11/2003 | Miller |
| 6,652,484 B1 | 11/2003 | Hunckler et al. |
| 6,655,655 B1 | 12/2003 | Matkovich et al. |
| 6,656,517 B2 | 12/2003 | Michal et al. |
| 6,665,888 B1 | 12/2003 | Kwak |
| 6,669,681 B2 | 12/2003 | Jepson et al. |
| 6,673,049 B2 | 1/2004 | Hommann et al. |
| 6,673,051 B2 | 1/2004 | Flinchbaugh |
| 6,695,817 B1 | 2/2004 | Fangrow, Jr. |
| 6,699,213 B1 | 3/2004 | Annis et al. |
| 6,706,022 B1 | 3/2004 | Leinsing et al. |
| 6,708,950 B2 | 3/2004 | Christensen et al. |
| 6,719,991 B2 | 4/2004 | Darouiche et al. |
| 6,726,672 B1 | 4/2004 | Hanly et al. |
| 6,730,107 B2 | 5/2004 | Kelley et al. |
| 6,733,000 B2 | 5/2004 | McCarty et al. |
| 6,733,461 B2 | 5/2004 | Ow |
| 6,733,481 B2 | 5/2004 | Ow |
| 6,745,998 B2 | 6/2004 | Doyle |
| 6,755,391 B2 | 6/2004 | Newton et al. |
| 6,780,497 B1 | 8/2004 | Walter |
| 6,802,836 B2 | 10/2004 | Bouphavichith et al. |
| 6,808,161 B1 | 10/2004 | Hishikawa |
| D500,132 S | 12/2004 | Peterson et al. |
| D500,133 S | 12/2004 | Peterson et al. |
| D500,552 S | 1/2005 | Peterson et al. |
| D500,853 S | 1/2005 | Peterson et al. |
| 6,840,501 B2 | 1/2005 | Doyle |
| 6,849,061 B2 | 2/2005 | Wagner |
| 6,889,437 B2 | 5/2005 | Bader et al. |
| 6,896,665 B2 | 5/2005 | Picha et al. |
| 6,897,349 B2 | 5/2005 | Gibbins et al. |
| 6,916,379 B2 | 7/2005 | Shekalim et al. |
| 6,936,031 B2 | 8/2005 | Caleffi |
| 6,972,001 B2 | 12/2005 | Emig et al. |
| 6,994,315 B2 | 2/2006 | Ryan et al. |
| 6,994,325 B2 | 2/2006 | Riedl |
| 7,004,923 B2 | 2/2006 | Deniega et al. |
| 7,004,934 B2 | 2/2006 | Vaillancourt |

(56) References Cited

U.S. PATENT DOCUMENTS

| | | |
|---|---|---|
| 7,008,407 B1 | 3/2006 | Kamp |
| 7,044,441 B2 | 5/2006 | Doyle |
| 7,048,724 B2 | 5/2006 | Grossman et al. |
| 7,048,962 B2 | 5/2006 | Shekalim et al. |
| 7,052,603 B2 | 5/2006 | Schick |
| 7,090,191 B2 | 8/2006 | Matkovich et al. |
| 7,094,218 B2 | 8/2006 | Rome et al. |
| 7,100,890 B2 | 9/2006 | Cote, Sr. et al. |
| 7,101,353 B2 | 9/2006 | Lui et al. |
| 7,112,177 B2 | 9/2006 | Christensen et al. |
| 7,147,138 B2 | 12/2006 | Shelton, IV |
| 7,150,740 B2 | 12/2006 | Bennett et al. |
| 7,163,495 B2 | 1/2007 | Fazio et al. |
| 7,165,568 B2 | 1/2007 | Kessell et al. |
| 7,179,244 B2 | 2/2007 | Smith et al. |
| 7,184,825 B2 | 2/2007 | Leinsing et al. |
| 7,207,946 B2 | 4/2007 | Sirokman |
| 7,303,553 B2 | 12/2007 | Ott |
| 7,311,690 B2 | 12/2007 | Burnett |
| 7,312,304 B2 | 12/2007 | Coy et al. |
| 7,314,061 B2 | 1/2008 | Peppel |
| 7,320,674 B2 | 1/2008 | Ruddell et al. |
| 7,341,240 B2 | 3/2008 | Ciesielka |
| 7,377,915 B2 | 5/2008 | Rasmussen et al. |
| 7,383,073 B1 | 6/2008 | Abovitz et al. |
| 7,396,348 B2 | 7/2008 | Newton et al. |
| 7,401,703 B2 | 7/2008 | McMichael et al. |
| 7,452,346 B2 | 11/2008 | Axelsson |
| 7,452,354 B2 | 11/2008 | Bright et al. |
| 7,468,058 B2 | 12/2008 | Kanie et al. |
| 7,497,848 B2 | 3/2009 | Leinsing et al. |
| 7,497,849 B2 | 3/2009 | Fangrow, Jr. |
| 7,524,311 B2 | 4/2009 | Phung et al. |
| 7,530,546 B2 | 5/2009 | Ryan et al. |
| 7,547,302 B2 | 6/2009 | Porto et al. |
| 7,563,243 B2 | 7/2009 | Mendels |
| 7,569,045 B2 | 8/2009 | Deniega et al. |
| 7,578,803 B2 | 8/2009 | Rome et al. |
| 7,584,767 B2 | 9/2009 | Funamura et al. |
| 7,591,805 B2 | 9/2009 | Lampropoulos |
| 7,594,910 B2 | 9/2009 | Butts et al. |
| 7,611,503 B2 | 11/2009 | Spohn et al. |
| 7,614,123 B2 | 11/2009 | Schweikert |
| 7,621,903 B2 | 11/2009 | Delegge |
| 7,628,774 B2 | 12/2009 | Fangrow, Jr. |
| 7,628,779 B2 | 12/2009 | Aneas |
| 7,632,260 B2 | 12/2009 | Antoine |
| 7,637,893 B2 | 12/2009 | Christensen et al. |
| 7,644,722 B2 | 1/2010 | Christensen et al. |
| 7,674,248 B2 | 3/2010 | Anderson et al. |
| 7,678,092 B2 | 3/2010 | Matloub et al. |
| 7,682,332 B2 | 3/2010 | Tanaka |
| 7,691,090 B2 | 4/2010 | Belley et al. |
| 7,695,458 B2 | 4/2010 | Belley et al. |
| 7,708,027 B2 | 5/2010 | Yokota et al. |
| 7,717,891 B1 | 5/2010 | Whaley |
| 7,726,315 B2 | 6/2010 | Field |
| 7,726,328 B2 | 6/2010 | Christensen et al. |
| 7,736,336 B2 | 6/2010 | Plilshka et al. |
| 7,744,594 B2 | 6/2010 | Yamazaki et al. |
| 7,766,304 B2 | 8/2010 | Phillips |
| 7,766,938 B2 | 8/2010 | McGurk et al. |
| 7,798,974 B2 | 9/2010 | Sirokman |
| 7,815,168 B2 | 10/2010 | Vangsness et al. |
| 7,824,384 B2 | 11/2010 | Watson, Jr. |
| 7,833,194 B2 | 11/2010 | Owens et al. |
| 7,854,731 B2 | 12/2010 | Rome et al. |
| 7,857,284 B2 | 12/2010 | Kimball et al. |
| 7,867,204 B2 | 1/2011 | Bartholomew et al. |
| 7,879,012 B2 | 2/2011 | Kane et al. |
| 7,892,181 B2 | 2/2011 | Christensen et al. |
| 7,924,255 B2 | 4/2011 | Hsu et al. |
| 8,007,257 B2 | 8/2011 | Heaton et al. |
| 8,048,046 B2 | 11/2011 | Hudspeth et al. |
| 8,048,056 B2 | 11/2011 | Picha et al. |
| 8,052,671 B2 | 11/2011 | Christensen et al. |
| 8,057,448 B2 | 11/2011 | Williams et al. |
| 8,074,848 B2 | 12/2011 | Pittl et al. |
| 8,083,332 B2 | 12/2011 | Price et al. |
| 8,177,772 B2 | 5/2012 | Christensen et al. |
| 8,210,166 B2 | 7/2012 | Denton et al. |
| 8,224,422 B2 | 7/2012 | Mottola et al. |
| 8,235,971 B2 | 8/2012 | Christensen et al. |
| 8,246,590 B2 | 8/2012 | Hu et al. |
| 8,337,475 B2 | 12/2012 | Christensen et al. |
| 8,435,221 B2 | 5/2013 | Hu et al. |
| 8,636,721 B2 | 1/2014 | Alam et al. |
| 8,814,839 B2 | 8/2014 | Christensen et al. |
| 9,295,764 B2 | 3/2016 | Christensen et al. |
| 9,393,353 B2 | 7/2016 | Alam et al. |
| 2001/0047158 A1 | 11/2001 | Ladd |
| 2002/0002351 A1 | 1/2002 | Cote et al. |
| 2002/0123715 A1 | 9/2002 | Sorenson et al. |
| 2002/0148467 A1 | 10/2002 | Bosse et al. |
| 2002/0153503 A1 | 10/2002 | Newton et al. |
| 2002/0198458 A1 | 12/2002 | Tripp et al. |
| 2003/0017920 A1 | 1/2003 | Fazio et al. |
| 2003/0032940 A1 | 2/2003 | Doyle |
| 2003/0040769 A1 | 2/2003 | Kelley et al. |
| 2003/0062498 A1 | 4/2003 | Decler et al. |
| 2003/0111121 A1 | 6/2003 | Skeens et al. |
| 2003/0159755 A1 | 8/2003 | Wessberg |
| 2003/0165647 A1 | 9/2003 | Kaneko et al. |
| 2003/0173536 A1 | 9/2003 | Christensen et al. |
| 2004/0049157 A1 | 3/2004 | Plishka et al. |
| 2004/0078026 A1 | 4/2004 | Wagner |
| 2004/0082923 A1 | 4/2004 | Field |
| 2004/0116894 A1 | 6/2004 | Delegge |
| 2004/0209801 A1 | 10/2004 | Brand et al. |
| 2004/0215155 A1 | 10/2004 | Wolfe et al. |
| 2004/0232696 A1 | 11/2004 | Andre |
| 2004/0267163 A1 | 12/2004 | Opie et al. |
| 2005/0000975 A1 | 1/2005 | Carco et al. |
| 2005/0025816 A1 | 2/2005 | Tanaka |
| 2005/0090805 A1 | 4/2005 | Shaw et al. |
| 2005/0121638 A1 | 6/2005 | Doyle |
| 2005/0131357 A1 | 6/2005 | Denton et al. |
| 2005/0143691 A1 | 6/2005 | Picha et al. |
| 2005/0203463 A1 | 9/2005 | Lampropoulos |
| 2005/0203597 A1 | 9/2005 | Yamazaki et al. |
| 2005/0209572 A1 | 9/2005 | Rome et al. |
| 2005/0209581 A1 | 9/2005 | Butts et al. |
| 2005/0251102 A1 | 11/2005 | Hegland et al. |
| 2005/0261636 A1 | 11/2005 | Rome et al. |
| 2005/0261664 A1 | 11/2005 | Rome et al. |
| 2005/0267445 A1 | 12/2005 | Mendels |
| 2005/0267487 A1 | 12/2005 | Christensen et al. |
| 2005/0281822 A1 | 12/2005 | Cedarbaum et al. |
| 2006/0009801 A1 | 1/2006 | McGurk et al. |
| 2006/0015086 A1 | 1/2006 | Rasmussen et al. |
| 2006/0025816 A1 | 2/2006 | Shelton |
| 2006/0058702 A1 | 3/2006 | Christensen et al. |
| 2006/0079853 A1 | 4/2006 | Christensen et al. |
| 2006/0092109 A1 | 5/2006 | Hsu et al. |
| 2006/0116721 A1 | 6/2006 | Yun et al. |
| 2006/0118749 A1 | 6/2006 | Ryan et al. |
| 2006/0129109 A1 | 6/2006 | Shaw et al. |
| 2006/0200089 A1 | 9/2006 | Lopez et al. |
| 2006/0211998 A1 | 9/2006 | Fangrow |
| 2006/0211999 A1 | 9/2006 | Fangrow |
| 2006/0212000 A1 | 9/2006 | Fangrow |
| 2006/0212001 A1 | 9/2006 | Fangrow |
| 2006/0212002 A1 | 9/2006 | Fangrow |
| 2006/0212003 A1 | 9/2006 | Fangrow |
| 2006/0264842 A1 | 11/2006 | Fangrow |
| 2007/0038143 A1 | 2/2007 | Christensen et al. |
| 2007/0073270 A1 | 3/2007 | Christensen et al. |
| 2007/0083157 A1 | 4/2007 | Belley et al. |
| 2007/0083162 A1 | 4/2007 | O'Reagan et al. |
| 2007/0100295 A1 | 5/2007 | Belley et al. |
| 2007/0100322 A1 | 5/2007 | Venugopalan et al. |
| 2007/0100324 A1 | 5/2007 | Tempel et al. |
| 2007/0235674 A1 | 10/2007 | Vangsness et al. |
| 2007/0235675 A1 | 10/2007 | Kimball et al. |

(56) References Cited

U.S. PATENT DOCUMENTS

| | | |
|---|---|---|
| 2007/0235676 A1 | 10/2007 | Vangsness et al. |
| 2007/0255167 A1 | 11/2007 | Christensen et al. |
| 2007/0255229 A1 | 11/2007 | Kane et al. |
| 2007/0260195 A1 | 11/2007 | Bartholomew et al. |
| 2007/0270764 A1 | 11/2007 | Gordon |
| 2007/0282268 A1 | 12/2007 | Mayse |
| 2008/0097407 A1 | 2/2008 | Plishka |
| 2008/0091174 A1 | 4/2008 | Alam et al. |
| 2008/0103408 A1 | 5/2008 | Denton et al. |
| 2008/0114316 A1 | 5/2008 | Christensen et al. |
| 2008/0277610 A1 | 11/2008 | Bahner et al. |
| 2009/0012493 A1 | 1/2009 | Harig |
| 2009/0043270 A1 | 2/2009 | Noyce et al. |
| 2009/0069763 A1 | 3/2009 | Dicarlo et al. |
| 2009/0142741 A1 | 6/2009 | Ault et al. |
| 2009/0219353 A1 | 9/2009 | Price et al. |
| 2009/0261130 A1 | 10/2009 | Pittl et al. |
| 2009/0312725 A1 | 12/2009 | Braga |
| 2009/0314973 A1 | 12/2009 | Christensen et al. |
| 2010/0030163 A1 | 2/2010 | Carrez et al. |
| 2010/0044609 A1 | 2/2010 | Matsubara |
| 2010/0274229 A1 | 10/2010 | Duocastella Codina et al. |
| 2011/0009849 A1 | 1/2011 | Christensen et al. |
| 2011/0022012 A1 | 1/2011 | Kerr et al. |
| 2011/0071415 A1 | 3/2011 | Karwoski et al. |
| 2011/0083665 A1 | 4/2011 | Denton et al. |
| 2011/0105963 A1 | 5/2011 | Hu et al. |
| 2011/0172510 A1 | 7/2011 | Chickering, III |
| 2011/0238022 A1 | 9/2011 | Massi et al. |
| 2011/0275964 A1 | 11/2011 | Greener |
| 2011/0276017 A1 | 11/2011 | Schuessler et al. |
| 2012/0220984 A1 | 8/2012 | Christensen et al. |
| 2013/0090614 A1 | 4/2013 | Christensen et al. |
| 2014/0182594 A1 | 7/2014 | Alam et al. |
| 2014/0358095 A1 | 12/2014 | Christensen et al. |

FOREIGN PATENT DOCUMENTS

| | | |
|---|---|---|
| DE | 9105229 | 6/1991 |
| DE | 4311715 | 10/1994 |
| EP | 0270205 | 6/1988 |
| EP | 0829248 | 3/1998 |
| EP | 1547537 | 6/2005 |
| EP | 1684824 | 8/2006 |
| EP | 1740253 | 1/2007 |
| EP | 1782850 | 5/2007 |
| FR | 2551978 | 3/1985 |
| GB | 2394761 | 5/2004 |
| JP | 2002049660 | 2/1990 |
| JP | 2005115556 | 5/1993 |
| JP | H6504468 | 5/1994 |
| JP | H666642 | 9/1994 |
| JP | 2000517216 | 12/2000 |
| JP | 2002177379 | 6/2002 |
| WO | 1990003194 | 4/1990 |
| WO | 1992007591 | 5/1992 |
| WO | 1995001135 | 1/1995 |
| WO | 1999011192 | 3/1999 |
| WO | 200204065 | 1/2002 |
| WO | 2002004065 | 1/2002 |
| WO | 2003001993 | 1/2003 |
| WO | 2003018105 | 3/2003 |
| WO | 2005007213 | 1/2005 |
| WO | 2005044716 | 5/2005 |
| WO | 2005052366 | 6/2005 |
| WO | 2005099805 | 10/2005 |
| WO | 2005107843 | 11/2005 |
| WO | 2006004943 | 1/2006 |
| WO | 2006055288 | 5/2006 |
| WO | 2006060248 | 6/2006 |
| WO | 2006066023 | 6/2006 |
| WO | 2007038643 | 4/2007 |
| WO | 2007116386 | 10/2007 |
| WO | 2008115439 | 9/2008 |
| WO | 2008142580 | 11/2008 |
| WO | 2009027665 | 3/2009 |
| WO | 2009081180 | 7/2009 |
| WO | 2009118521 | 10/2009 |
| WO | 2010028044 | 3/2010 |
| WO | 2010091356 | 8/2010 |
| WO | 2011107972 | 9/2011 |

OTHER PUBLICATIONS

Office Action dated Oct. 1, 2010 for U.S. Appl. No. 10/595,450.
Office Action dated Oct. 6, 2015 for U.S. Appl. No. 12/188,955.
Office Action dated Oct. 30, 2008 for U.S. Appl. No. 10/595,450.
Office Action dated Oct. 30, 2008 for U.S. Appl. No. 11/248,082.
Office Action dated Oct. 30, 2015 for U.S. Appl. No. 14/162,654.
Office Action dated Nov. 6, 2013 for U.S. Appl. No. 12/188,955.
Office Action dated Dec. 10, 2014 for U.S. Appl. No. 12/188,955.
Office Action dated Dec. 21, 2010 for U.S. Appl. No. 11/248,082.
Office Action dated Dec. 24, 2013 for U.S. Appl. No. 13/688,000.
Office Action dated Jul. 7, 2011 for U.S. Appl. No. 11/535,245.
AstraTech Healthcare, 'Premimiun Wound Drainage Products', http://surgery.astratech.com/Main.aspx?Item-155788&navl=5&navl=82118&nava=81296, Copyright ,2010.
Bard Access Systems, Inc., 'Poly Per-Q-Cath PICC Catheter with Safety Excallibur Introducer', Instructions for Use, , May 2003.
Bard, 'Groshong NXT PICC Instructions for Use', Product Brochure, ,Nov. 2003.
Denver Biomedical, 'Pleurx Drainage Kit Catalog No. 50-7500', Instructions for Use, No date available.
Experimental Plerueodesis in Rabbits Induced by Silver Nitrate or Talc, ASAP, vol. 199 No. 5 ,May 1, 2001 ,1516.
ICU-USA, 'Wound Drainage', www.icu-usa.com/tour/procedures/drains.htm, Copyright 1999-2004.
Iso 10079-2 Medical Suction Equipment—Part 2: Manually Powered Suction Equipment, International Standard Organization ,1999.
Management of Malignant Pleural Effusions, Am. J. Respir. Crit. Care Med., vol. 165 No. 5 ,2000 ,1987-2001.
Medcomp Ash II Split Cath™ 'Features and Benefits' Product Brochure, ,Oct. 1999.
Tremblay, et al.,Singel-Center Experience with 250 Tunnelled Pleural Catheter Insertions for Manignant Pleural Effusions, Chest, vol. 129 No. 2 ,2006 ,362-368.
Vargas, et al.,Comparison of Silver Nitrate and Tetracycline as Pleural Sclerosing Agents in Rabbits, Chest, vol. 108 No. 4 ,1995 ,1080-1083.
European Supplemental Search Report dated Aug. 17, 2012 for EP04811627.1.
International Search Report and Written Opinion dated Jan. 5, 2007 for PCT/US2006/037766.
International Search Report and Written Opinion dated Jul. 5, 2005 for PCT/US2004/38937.
Notice of Allowance dated Jan. 12, 2010 for U.S. Appl. No. 11/248,082.
Notice of Allowance dated Apr. 30, 2014 for U.S. Appl. No. 13/688,000.
Notice of Allowance dated Jun. 10, 2013 for U.S. Appl. No. 13/469,849.
Notice of Allowance dated Sep. 17, 2012 for U.S. Appl. No. 11/248,082.
Notice of Allowance dated Oct. 15, 2010 for U.S. Appl. No. 11/248,082.
Notice of Allowance dated Nov. 30, 2015 for U.S. Appl. No. 14/464,503.
Office Action dated Jan. 11, 2012 for U.S. Appl. No. 12/188,955.
Office Action dated Feb. 1, 2011 for U.S. Appl. No. 12/879,673.
Office Action dated Mar. 17, 2011 for U.S. Appl. No. 11/535,245.
Office Action dated Mar. 28, 2012 for U.S. Appl. No. 11/248,082.
Office Action dated Mar. 29, 2013 for U.S. Appl. No. 12/188,955.
Office Action dated Apr. 9, 2010 for U.S. Appl. No. 10/595,450.
Office Action dated Apr. 23, 2013 for U.S. Appl. No. 13/677,000.
Office Action dated Apr. 23, 2013 for U.S. Appl. No. 13/688,000.
Office Action dated May 2, 2014 for U.S. Appl. No. 12/188,955.
Office Action dated May 4, 2016 for U.S. Appl. No. 12/188,955.
Office Action dated May 26, 2011 for U.S. Appl. No. 12/188,955.

(56) References Cited

OTHER PUBLICATIONS

Office Action dated Jun. 9, 2015 for U.S. Appl. No. 14/464,503.
Office Action dated Jun. 12, 2013 for U.S. Appl. No. 10/595,450.
Office Action dated Jul. 6, 2011 for U.S. Appl. No. 11/248,082.
Office Action dated Jul. 13, 2012 for U.S. Appl. No. 12/188,955.
Office Action dated Jul. 17, 2009 for U.S. Appl. No. 10/595,450.
Office Action dated Jul. 25, 2017 for U.S. Appl. No. 15/081,783.
Office Action dated Aug. 1, 2012 for U.S. Appl. No. 13/469,849.
Office Action dated Aug. 2, 2013 for U.S. Appl. No. 13/688,000.
Office Action dated Aug. 23, 2011 for U.S. Appl. No. 12/879,673.
Pleural Disease—Diagnosis and Management, The Practitioner ,May 1999 ,412.
Pleurodesis, ASAP, vol. 118, No. 3 ,Sep. 1, 2000 ,577.
Bellamy, et al.,The Causes of Death in Conventional Land Warfare: Implications for combat Casualty Care Research, Mil. Med., vol. 149 ,1984 ,55-62.
Bilski, et al.,Battlefield Casualties Treated at Camp Rhino, Afghanistan: Lessons Learned, J. Trauma, vol. 54 No. 5 , May 2003 ,814-822.
Campisi, et al.,Outpatient Treatment of Spontaneous Pheumothorax in a Community Hospital Using a Heimlich Flutter Valve: A Case Series, The Journal of Emergency Medicine, vol. 15 No. 1 ,1997 , 115-119.
Groves Jr., et al.,Operations in Urban Environments, Military Review, vol. 78 No. 4 ,Jul./Aug. 1998.
Heimlich, et al.,Valve Drainage of the Pleural Cavity, Diseases of the Chest, vol. 53 No. 3 ,1968 ,282-287.
Hewitt, et al.,A Management Strategy for Malignancy-Induced Pleural Effusion: Long-Term Thoracostomy Drainage, ONF, vol. 14 No. 5 ,1987 ,17-22.
Jaskille, et al.,A Portable Handpump is Effective inthe Evacuation of Hemothorax in a Swine Model of Penetratine Chest Injury, The Journal of Trauma Injury, Infection, and Critical Care ,Nov. 2003 ,864-868.
Light,R.W. et al.,A Single Intrapleural Injection of Transforming Growth Factor-Beta(2) Produces an Excellent Pleurodesis in Rabbits, Am. J. Respir. Crit. Care Med., vol. 162 No. 1 ,2000 ,98-104.
Light, et al.,A Single Intrapleural Injuection of Transforming Growth Factor-Beta(2) Produces an Excellent Pleurodesis in Rabbits, Am. J. Respir. Crit, Care Med., vol. 162, No. 1 ,2000 ,98-104.
Light, et al.,Talc Slurry is an Effective Pleural Sclerosant in Rabbits, Chest, vol. 106 No. 6 ,1995 ,1702-1706.
Lodi, et al.,A New Portable Chest Drainage Device, Ann, Thorac. Surg., vol. 69 ,2000 ,998-1001.
Mabry, et al.,United States Army Rangers in Somalia: An Analysis of Combat Casualties on an Urban Battlefield, J. Trauma, vol. 49 No. 3 ,Sep. 2000 ,515-529.
Medcompare, et al.,Drains with Reservoirs, General Surgery Product Matrix, Medcompare.com/matrix/1885/Drains-with-Reservoirs.html, Copyright ,2003-2010 ,198-202.
Milton Jr., et al.,Urban Operations: Future War, Military Review, vol. 74 Issue 2 ,Feb. 1994.
Montes, et al.,Influence of Talc Dos on Extrapleural Talc Dissemination after Talc Pleurodesis, Am. J. Respir, Crit. Care Med., vol. 168 No. 3 ,2003 ,348-355.
Ohm, et al.,Use of Indwelling Pleural Catheter Compared wtih Thorascopic Talc Pleurodesis in teh Management of Malignant Peural Effusions, Division of Thoracic Surgery and Department of Surgery, William Beaumont Hospital, The American Surgeon ,Mar. 2003 ,198-202.
Pope, et al.,Fluid Resuscitation: State fo the Science for Treating Combat Casualties and Civilian Injuries, National Academy Press ,1999.
Schweitzer, et al.,Use of Heimlich Valve in compact Autotransfusion Device, The Journal of Trauma, vol. 27 No. 5 ,1987 ,537-542.

PORTABLE HAND PUMP FOR EVACUATION OF FLUIDS

PRIORITY

This application is a continuation of U.S. patent application Ser. No. 15/210,787, filed Jul. 14, 2016, now U.S. Pat. No. 9,907,887, which is a division of U.S. patent application Ser. No. 14/162,654, filed Jan. 23, 2014, now U.S. Pat. No. 9,393,353, which is a division of U.S. patent application Ser. No. 10/595,450, now U.S. Pat. No. 8,636,721, filed as a U.S. national stage application under 35 U.S.C. § 371 of International Application No. PCT/US04/38937, filed Nov. 20, 2004, which claims priority to U.S. Provisional Application No. 60/523,321, filed Nov. 20, 2003, each of which is incorporated by reference in its entirety into this application.

BACKGROUND OF THE INVENTION

1. Field of the Invention

The present invention relates to pumps for removing fluids from a body cavity of a subject. More particularly, the invention relates to a manually operated pump that can be used to remove fluids from a subject suffering from hemopneumothorax.

2. Background of the Technology

Penetrating chest injuries have been a major cause of death on the battlefield.[1] Injured soldiers with hemopneumothorax need treatment as soon as possible. The possibility of rapidly moving front lines and urban environment combat may preclude rapid transportation of wounded soldiers to higher echelons of medical care.[2,3,4] The conventionally used equipment for the evacuation of blood and air from the pleural space of a subject is a large-bore thoracostomy tube connected to negative-pressure water seal devices, for example Pleur-Evac® (Deknatel Division of Pfizer, Corp.). Such currently available drainage systems are cumbersome, bulky, and difficult to manage during transport of the wounded soldier. Furthermore, continuous suction for the drainage system is seldom available under field conditions. Historically penetrating chest injuries resulting in pneumothorax[5] have been common. Such conditions have fortunately seen some decreases due to the use of body armor by soldiers[6]. Emergency treatment of such traumatic chest injuries does, however remain a major medical problem. Although one-way valves such as the Heimlich valves can be used and have been shown to be effective for simple pneumothorax[7,8,9,10] one distinct disadvantage is that by design such valves rely on gravity or increased intrathoracic pressure for drainage and do not provide suction to facilitate the evacuation of blood/clots and the re-expansion of the injured lung.

There exists therefore a need for a manually operated pump that can provide effective suction to remove fluids from a subject and more particularly to facilitate the effective treatment of traumatic hemopneumothorax in patients in an emergency/field environment where continuous suction is not available or easily employed.

SUMMARY OF THE INVENTION

The present invention provides a manually operable pump that can be quickly and easily employed under emergency or field conditions to remove fluids from a subject.

Also provided is an effective manually operable pump that can be used to remove fluids in the treatment of a subject suffering from hemopneumothorax.

Also provided is an effective pumping device that can by intermittent manual actuation effectively remove blood, blood clots, fluid, and air from a body cavity.

Also provided is a manually operable pump that is adapted for attachment to an intake fluid conduit and an outlet fluid conduit to facilitate the removal of fluid from a subject.

Also provided is a manually operable pump that is adapted for attachment and use with a range of conduits such as a standard pleural tube, a standard endotracheal tube, and an indwelling catheter for the effective removal of fluids and/or blood clots and air from the body cavity of a subject.

Also provided is a manually operable pump having one-way valves that serve to direct the movement of fluid in only one direction when the pump is manually activated.

Also provided is a manually operable pump for the removal of fluids from a body cavity of a subject, the manual operation being accomplished by contact with any limb or body part of the operator.

Also provided is a manually operable pump that is configured to be selectively connected to an autotransfusion device.

Also provided is a manually operable pump having one-way valves of such sensitivity that the valves can effectively direct the movement of fluid in only one direction without manual activation and with the aid of gravity flow alone.

Also provided is a manually operable pump that effectively removes blood, blood clots, fluid, and air from a body cavity without the aid of wall suction, rigid containers, water-seal devices, or electricity.

Also provided is a system of manually operable pumps, which can be connected as multiple successive pumps to effectively remove blood, blood clots, fluid, and air from a body cavity.

Also provided is a manually operable pump that effectively removes blood, blood clots, fluid, and air from a body cavity, the pump generating a negative pressure in the range of 5 mm to 100 mm Hg.

DETAILED DESCRIPTION OF THE INVENTION

At present, manual suction devices are not available for use during the care and initial treatment of a subject in an emergency situation. Such a device would be particularly useful in providing emergency care for combat casualties, who frequently are in danger of serious injury or death due to traumatic hemopneumothorax. A manually operated pump that can evacuate blood or air from the throat, air passages, or chest would be most beneficial in the treatment of casualties who have suffered injuries to the chest. The pumping device of the present invention can also be adapted for other medical treatment uses such as, for example, checking correct placement of an endotracheal tube (tube placed in the wind pipe) and evacuating secretions from the nose, mouth, and air passages or to evacuate fluids out of drains that have been placed into various body cavities during surgery. The manufacture and design of the pump is such that it can be sterilized and repeatedly reused or it can be cost-effectively produced so as to be disposed of after only one use.

Currently, electrical or battery operated suction devices are available but due to the austere environment often faced by the military, having a suction device that does not have to rely on electricity or batteries would be of benefit, especially when transporting the patient. Such conventional devices typically use a water seal as a one way valve and drainage is passive unless the system is connected to a suction source. The electrical suction devices available in the market are cumbersome and not suitable for use in the military environment and during transportation. Further, such devices can suddenly be of no use if the power supply to the conventional device is interrupted. Other one way valves are in existence but again they rely on gravity or increased pressure in the chest to help push out undesired air or fluids. The present invention provides a manually operable suction device that can pump large volumes of fluid (such as blood, water, mucus, blood clots, air, etc.) from a body cavity of a subject suffering from serious conditions brought on by chest injuries or other traumatic conditions where a manually operable pump would have potential life-saving benefit.

Unlike conventional devices and the standard of care currently provided for the removal of fluids from the body cavity of a subject, the present invention is not cumbersome, bulky, dependent on electrical powered wall suction or battery operated suction. Further it is small, simply configured and easy to transport under extreme, emergency, or combat conditions. Further, unlike the conventionally used Heimlich valves, which rely on gravity or increased intrathoracic pressure for drainage, and do not provide suction to facilitate evacuation of blood/clots and re-expansion of the injured lung, the present invention can provide very effective removal of fluid, blood clots and air from the body cavity of a subject.

Figure 1:
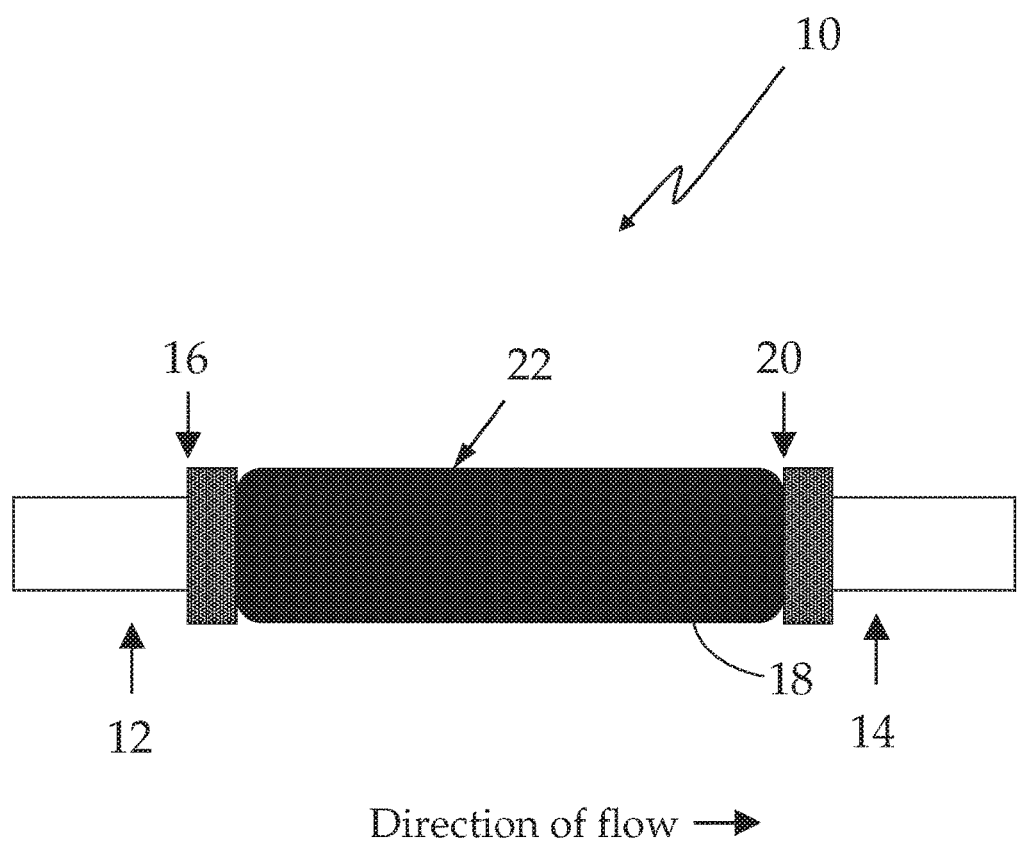
FIG. 1 provides a planar view of a basic embodiment of the manually operable pump of the present invention.

As shown in FIG. 1, the small, portable, easy to use manual pump (10) of the present invention can be adapted for attachment to virtually any usable fluid conduit as an inflow conduit (12) or an outflow conduit (14). Importantly, proximate to the connection of the inflow conduit (12), the pump of the present invention is provided with a one-way inflow valve (16) that acts to permit flow of fluids, blood clots, and air from the inflow conduit (12) into the interior of the pump (18) but limits or restricts any back flow of the same into the inflow conduit (12). Similarly, proximate to the connection of the outflow conduit (14), a one-way outflow valve (20) permits flow of fluids, blood clots, and air out of the pump interior (16) and into and through the lumen of the outflow conduit (14). This outflow one-way valve (20) also serves to limit or restrict the back flow of fluids from the outflow conduit into the pump interior (18). The one-way valves used in the present invention can be of any conventional configuration known for one-way flow valves and can be selected to be of such sensitivity that the pump device can be positioned so as to permit passage of fluid through the device by force of gravity alone if desired.

The pump (10) can be constructed of any material strong enough to withstand repeated manual compressions, flexible enough to facilitate easy manual use by the operator in compressing the body (22) of the pump, durable over prolonged and repeated usage, and fluid-tight so as to prohibit any leakage during use. The material used in the manufacture of the cylindrical bladder of the body (22) of the pump can be a natural, synthetic, or blended material suitable for the operational demands of the manually operable pump. The materials used in the manufacture of the pump can be of the nature to withstand sterilization and repeated uses or can be more cost-effectively manufactured for single use and disposal.

The manually operable pump of the present invention is very adaptable and is particularly well suited for connection to well known and commonly used thoracostomy tubes, endotracheal tubes or catheters, which are readily available to emergency medical practitioners or military field medics or corpsmen. This simple design, light weight transportability, and adaptability to many fluid conduits as needed offers a major logistical advantage in austere environments.

In addition to its usefulness to emergency military medical needs, the present invention offers additional logistical advantages of requiring no wall suction, rigid containers, water or electricity makes the present invention a very useful device for civilian applications, such as for civilian ground ambulance or medical helicopter transport emergency suction needs. Further, the device is also adaptable in that the outflow conduit can be connected to an autotransfusion unit if needed. Indeed, any circumstance where a manually operable pump is needed could be met by the device of the present invention.

Example

A test example of the device of the present invention was prepared by providing two pieces of clear vinyl tubing (4 inches in length and ½ inch inside diameter), which were connected to a cylindrical rubber bladder (1.5×3 inch) using adaptors and two one-way valves. The position of the one-way valves on both ends of the rubber bladder ensured that fluid could only move in one direction on squeezing the bladder (FIG. 1). The inflow vinyl tubing was attached to the pleural evacuation tube whereas the outflow tubing was attached to a collection bag for the measurement of evacuated blood.

A swine model of penetrating chest injury was designed to test the concept of the present invention. The purpose of the test was to compare the effectiveness of operation of the manually operable pump of the present invention to the conventional device and accepted standard of care for the evacuation of a large hemopnenmothorax. The present invention pump was tested in a swine model of penetrating chest injury and bleeding in the pleural space. Table 1 provides the test data obtained for test groups 1, 2, and 3. Test Group 1, was a conventional standard of care model. Test Group 2 was the manually operable pump of the present invention connected to a conventionally used chest tube. Test Group 3, was designed to demonstrate the adaptability of the present invention in that the manually operable hand pump was connected to an endotracheal tube rather than the conventionally used chest tube. As can be seen in the data of Table 1, overall, the manually operable pump performed better than the standard of care and was also shown to be very effective when connected to a conventional chest tube or an endotracheal tube.

Figure 2:
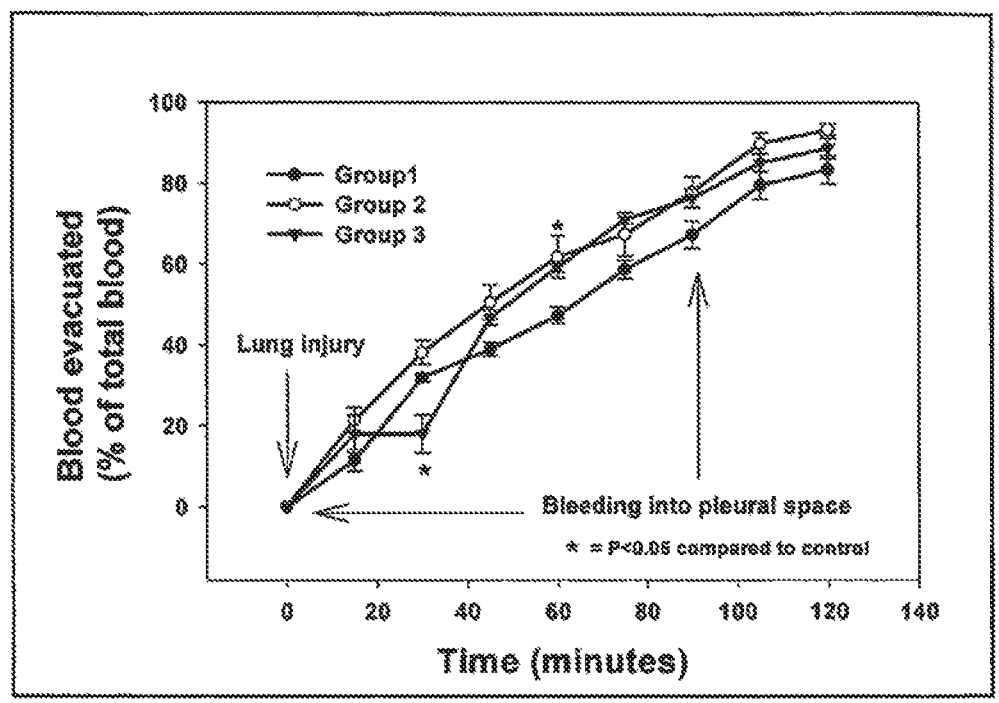
FIG. 2 shows the comparative experimental results of a conventional device employing the standard of care for treating hemopneumothorax as compared to the operational results obtained by use of the manually operable pump of the present invention employing a standard pleural tube in one case and the manually operable pump of the present invention using a standard endotracheal tube in a second case.

The results of the comparative tests are summarized and graphically displayed in FIG. 2. In addition, it was found that the device of the present invention was able to pump water at a maximum rate of 1 L/minute. The negative pressure generated in the pleural tube (in vivo) was affected by the rate of pumping.

Notably, a single pump generated negative pressure of 12 mmHg and it was found that multiple successive pumps could generate a maximum pressure of −80-90 mmHg.

The present invention can be manually operate by compression of the pump body (22) by any manual means; that is, it is within the concept of the invention that the pump can be sized and configured to be pump by hand compression using only one hand, it can be configured slightly larger to be compressed by an operator with both hands, it can also be sized, shaped, and even externally textured to avoid slippage and made compressible by foot or pedal activation. Any body part can be used to compress the body (22) of the present invention and remain within the concept of the present invention. Further, any shape, construction, material, or size of conduit for the inflow and outflow conduits can be used within the concept of the present invention.

The adaptability of the present invention permits that the device can be so positioned as to permit fluid transport through the one-way valves and through the pump by use of gravity powered flow alone. It is also within the concept of the invention that the manually operable pump can be configured to be selectively connected to an autotransfusion device. Further, it is possible in the present invention to attach suction handles to suck out secretions from the mouth, checking for correct tube placement when a tube must be properly positioned in the windpipe, and to suck fluids out of drains, catheters, or other conduits, which have been placed surgically.

REFERENCES

1. Pope, A; French, G.; Longnecker, D. eds.; Fluid Resuscitation: State of the Science for Treating Combat Casualties and Civilian Injuries., Washington, D.C., National Academy Press: 1999:9-16.
2. Groves, J; Operations in Urban Environments, Mil. Rev. 1998: July-August 31-40.
3. Milton, T R.; Urban Operations: Future War, Mil. Rev. 1994: February 37-46.
4. Mabry, R L; Holcomb, J B; Baker, A M; et al. United States Army Rangers in Somalia: An Analysis of Combat Casualties on an Urban Battlefield, J. Trauma, 2000; 49:515-529.
5. Bellamy, R F; The Causes of Death in Conventional Land Warfare: Implications for Combat Casualty Care Research, Mil. Med. 1984; 149:55-62.
6. Bilski, T; Baker, B; Grove, J R; Battlefield Casualties Treated at Camp Rhino, Afghanistan: Lessons Learned, J. Trauma, 2003; 54:814-821.
7. Heimlich, H J; Valve Drainage of the Pleural Cavity. Dis. Chest. 1968; 53:282-287.
8. Campisi, P; Voitk, A J; Outpatient Treatment of Spontaneous Pneumothorax in a Community Hospital Using a Heimlich Flutter valve: A Case Series, J. Emerg. Med. 1997:15:115-119.
9. Lodi, R; Stefani, A; A New Portable Chest Drainage Device, Ann. Thorac. Surg., 2000; 69:998-1001.
10. Schweitzer, E F; Hauer, J M; Swan, K G; et al., Use of Heimlich Valve in Compact Autotransfusion Device. J. Trauma. 1987; 27:537-542.

What is claimed is:

1. A manually operable pump for removing fluids from a body cavity of a subject, the pump comprising:
   a fluid-tight pump body having a first end and a second end with a compressible center portion disposed between the first end and second end;
   an inflow connector attached to the first end, the inflow connector adaptable for connection to an inflow conduit;
   an inflow one-way valve disposed between the inflow connector and the pump body, the inflow one-way valve adapted to permit flow of fluid from the inflow conduit through the inflow connector and into the pump body but restricting backflow of fluid from the pump body into the inflow connector and inflow conduit; and
   wherein the inflow one-way valve allows fluid passage through the inflow valve when the pump is so positioned such that all power for fluid flow is provided by gravity alone.

2. The manually operable pump according to claim 1, further comprising:
   an outflow connector attached to the second end, the outflow connector adaptable for connection to an outflow conduit; and
   an outflow one-way valve disposed between the pump body and the outflow connector, the outflow one-way valve adapted to permit flow of fluid from the pump body into the outflow connector and into the outflow conduit but restricting backflow of fluid from the outflow conduit and outflow connector into the pump body;
   wherein the outflow one-way valve allows fluid passage through the outflow valve when the pump is so positioned such that all power for fluid flow is provided by gravity alone.

3. The manually operable pump according to claim 1, wherein the inflow conduit is selected from the group consisting of a pleural evacuation tube, a standard chest tube, an endotracheal tube, and a catheter.

4. The manually operable pump according to claim 1, wherein the compressible center portion is sized and configured to be compressed for effective pump operation by an operator using only one hand to initiate unidirectional fluid flow.

5. The manually operable pump according to claim 1, wherein the compressible center portion is sized and configured to be compressed for effective pump operation by an operator or operators using two hands to initiate unidirectional fluid flow.

6. The manually operable pump according to claim 1, wherein the compressible center portion is sized, shaped, and configured to be compressed for effective pump operation by an operator using foot compression on the center portion to initiate unidirectional fluid flow.

7. The manually operable pump according to claim 1, wherein the exterior of the compressible center portion is at least partially covered by a textured surface.

8. The manually operable pump according to claim 1, wherein the pump is effective in removing fluids, blood clots, or air from the body cavity of the subject suffering from hemopneumothorax.

9. The manually operable pump according to claim 1, wherein the pump is adapted to be connected to an autotransfusion device.

10. The manually operable pump according to claim 1, adapted for connection to at least one additional manually operable pump in series so as to provide a manually operable pump system.

11. The manually operable pump according to claim 1, wherein the pump effectively removes blood, blood clots, fluid, or air from the body cavity, the pump generating a negative pressure in a range of 5 mm Hg to 100 mm Hg.

12. A system for removing fluids from a body cavity, comprising:
    a fluid receptacle for receiving the fluids from the body cavity;
    a manually operable pump in fluid communication with both the body cavity and the fluid receptacle;
    an inflow connector adaptable for connecting the pump to an inflow conduit; and
    an inflow one-way valve disposed between the inflow connector and the pump, operation of the pump generating a negative pressure relative to the body cavity to transfer fluid from the body cavity to the fluid receptacle;
    wherein the pump is so positioned such that all power for fluid flow is provided by gravity.

13. The system according to claim 12, wherein the manually operable pump comprises a pump body interposed between two one-way valves, compression of the pump body initiating unidirectional fluid flow from the body cavity to the fluid receptacle.

14. The system according to claim 12, further comprising an implantable catheter in fluid communication with the manually operable pump.

15. The system according to claim 12, further comprising:
    an outflow conduit coupled to the fluid receptacle; and
    an outflow connector coupled to the outflow conduit and the manually operable pump.

16. The system according to claim 12, wherein the manually operable pump generates a fluid flow of up to one liter per minute.

17. The system according to claim 12, further comprising suction handles that are attachable to the manually operable pump to suck out secretions from a mouth.

18. A method of removing fluid during a medical procedure, comprising:
    attaching a manually operable pump to a proximal end of an inflow conduit, the manually operable pump in fluid communication with a fluid receptacle;
    generating a negative pressure via the manually operable pump to initiate fluid flow from the inflow conduit toward the fluid receptacle; and
    positioning the manually operable pump to flow fluid from the inflow conduit to the fluid receptacle such that all power for further fluid flow is provided by gravity.

19. The method according to claim 18, wherein the step of generating a negative pressure comprises compressing a pump body to initiate unidirectional fluid flow from a body cavity to the fluid receptacle.

20. The method according to claim 18, wherein the step of generating a negative pressure comprises compressing the pump body by hand or foot to initiate unidirectional fluid flow from the body cavity to the fluid receptacle.

* * * * *